(12) United States Patent
Schmelebeck et al.

(10) Patent No.: US 9,643,909 B2
(45) Date of Patent: May 9, 2017

(54) PROCESS FOR HYDROLYZING 1,2,4-TRIHALOBENZENE

(71) Applicant: BASF SE, Ludwigshafen (DE)

(72) Inventors: Gerald Schmelebeck, Buna, TX (US); Junmin Ji, Beaumont, TX (US); Eric George Klauber, Bad Duerkheim (DE); Michael Rack, Eppelheim (DE); Thomas Zierke, Boehl-Iggelheim (DE); Nicole Holub, Mannheim (DE); David Cortes, Quincy, IL (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/026,715

(22) PCT Filed: Sep. 25, 2014

(86) PCT No.: PCT/EP2014/070509
§ 371 (c)(1),
(2) Date: Apr. 1, 2016

(87) PCT Pub. No.: WO2015/049160
PCT Pub. Date: Apr. 9, 2015

(65) Prior Publication Data
US 2016/0251294 A1   Sep. 1, 2016

Related U.S. Application Data

(60) Provisional application No. 61/886,667, filed on Oct. 4, 2013.

(30) Foreign Application Priority Data

Oct. 31, 2013 (EP) .................................... 13191083

(51) Int. Cl.
| | | |
|---|---|---|
| *C07C 69/00* | (2006.01) | |
| *C07C 51/09* | (2006.01) | |
| *C07C 37/02* | (2006.01) | |
| *C07C 51/15* | (2006.01) | |
| *C07C 51/367* | (2006.01) | |
| *C07C 67/00* | (2006.01) | |
| *C07F 1/00* | (2006.01) | |
| *A01N 37/40* | (2006.01) | |

(52) U.S. Cl.
CPC .............. *C07C 51/09* (2013.01); *C07C 37/02* (2013.01); *C07C 51/15* (2013.01); *C07C 51/367* (2013.01); *C07C 67/00* (2013.01); *C07F 1/005* (2013.01); *A01N 37/40* (2013.01)

(58) Field of Classification Search
CPC ....... C07C 37/02; C07C 51/15; C07C 51/367; C07C 39/30; C07C 65/05; C07C 65/21; C07C 51/09; C07C 67/00; A01N 37/40; C07F 1/005
See application file for complete search history.

(56) References Cited

U.S. PATENT DOCUMENTS 4,094,913 A * 6/1978 Carlson .................... C07C 37/02
568/778

OTHER PUBLICATIONS

Written Opinion PCT/EP2014/070509 filed Apr. 1, 2016 (filed by applicant).*

* cited by examiner

*Primary Examiner* — Yevegeny Valenrod
*Assistant Examiner* — Blaine G Doletski
(74) *Attorney, Agent, or Firm* — Brinks Gilson & Lione

(57) ABSTRACT

The present invention relates to a process for providing a compound of formula (I):

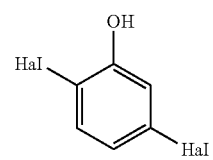

wherein Hal is a halogen, the process comprising the step of: reacting a compound of formula (II)

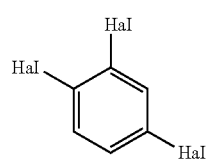

wherein Hal is defined as above, with an alkali metal sulfite of the formula $X_2SO_3$ and an alkali metal hydroxide of the formula YOH, wherein X and Y are independently selected from an alkali metal.

19 Claims, No Drawings

PROCESS FOR HYDROLYZING 1,2,4-TRIHALOBENZENE

This application is a National Stage application of International Application No. PCT/EP2014/070509, filed Sep. 25, 2014, which claims the benefit of U.S. Provisional Application No. 61/886,667, filed Oct. 4, 2013. This application also claims priority under 35 U.S.C. §119 to European Patent Application No. 13191083.8, filed Oct. 31, 2013.

The present invention relates to a process for hydrolyzing 1,2,4-trihalobenzene. The process according to the present invention can be carried out in the absence of organic solvents. In one embodiment, the present invention provides a process for obtaining 2,5-dichlorophenol by hydrolyzing 1,2,4-trichlorobenzene. 2,5-Dichlorophenol is an important intermediate in the production of the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid. The estimated global demand for dicamba in 2012 was about 12.000 metric tons per year. However, it is expected that the global demand for dicamba will increase significantly.

Dicamba is typically produced on an industrial scale via 2,5-dichlorophenol and using carboxylation under Kolbe-Schmitt conditions, methylation and subsequently saponification/acidification. 2,5-Dichrophenol in turn can be obtained from 1,4-dichlorobenzene or 1,2,4-trichlorobenzene. A synthetic route via 1,4-dichlorobenzene involving nitration and subsequent diazotation may, however, be undesired for use on an industrial scale. A synthetic route via 1,2,4-trichlorobenzene may suffer from limited availability of this starting material and from the formation of several byproducts which are formed in the synthesis of 2,5-dichlorophenol.

There is a need in the art for an efficient process for obtaining 2,5-dihalogen substituted phenols, such as 2,5-dichlorophenol.

SUMMARY OF THE INVENTION

The object of the present invention is to meet the above need. In particular, it is an object of the present invention to provide a process for obtaining 2,5-dihalogen substituted phenols such as 2,5-dichlorophenol with improved regioselectivity. It is a further object of the present invention to implement the improved process for the synthesis of dicamba on an industrial scale. In this context it should be noted that even minor improvements in the yield and/or 2,5-regioselectivity in reaction sequences for obtaining dicamba would provide a tremendous benefit. For example, an improvement of yield and/or 2,5-regioselectivity of 1% would provide an additional annual amount of 120 metric tons of dicamba.

The present invention relates to a process for hydrolyzing 1,2,4-trihalobenzene to obtain a compound of formula (I):

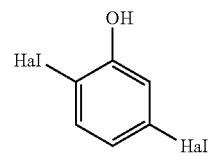

wherein Hal is a halogen atom.

In particular, the present invention is directed to a process for providing the above compound of formula (I), comprising the step of: reacting a compound of formula (II)

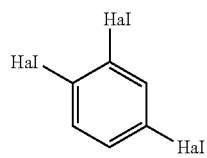

wherein Hal is defined as above, with an alkali metal sulfite of the formula $X_2SO_3$ and an alkali metal hydroxide of the formula YOH, wherein X and Y are independently selected from an alkali metal.

When reacting a compound of formula (II) with an alkali metal sulfite of the formula $X_2SO_3$ and an alkali metal hydroxide of the formula YOH as described above the alkali metal phenolate of formula (I) may be obtained, e.g. a sodium phenolate of formula (I) or a potassium phenolate of formula (I). Such an alkali metal phenolate of formula (I) may then be converted into the compound of formula (I) by adding an acid, such as $H_2SO_4$ or HCl. The pH in such an acidification step may be 1.5 or less.

The above process can be carried out in the substantial or complete absence of organic solvents. The use of organic solvents may be undesired e.g. from an environmental point of view. Furthermore, the process may be carried in the presence of water. Optionally, minor amounts of a $C_1$-$C_4$ alcohol may further be present. In some embodiments, the process is carried out in the absence of organic solvents apart from the optional presence of minor amounts of a $C_1$-$C_4$ alcohol. In other embodiments, the process is carried out in the complete absence of organic solvents.

Conventional processes for hydrolyzing 1,2,4-trihalobenzene are typically carried out using an alkali metal hydroxide such as NaOH, and a large excess of an alcoholic solvent such as methanol. Such reaction may result in a mixture of different regioisomers, e.g. 2,5-regioisomers, 2,4-regioisomers, and 3,4-regioisomers, and derivatives as defined in further detail below.

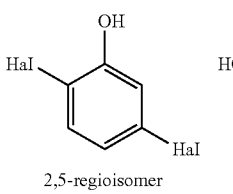
2,5-regioisomer

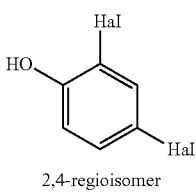
2,4-regioisomer

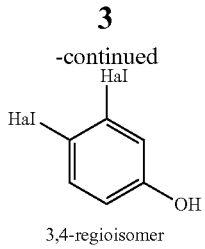

3,4-regioisomer

For example, hydrolyzing 1,2,4-trichlorobenzene in methanol using NaOH may result in a mixture of 2,5-dichlorophenol, 2,4-dichlorophenol, 3,4-dichlorophenol, 2,5-dichlorophenol methyl ether, 2,4-dichlorophenol methyl ether, and 3,4-dichlorophenol methyl ether. In view of the role of 2,5-dichlorophenol as an intermediate in the synthesis of dicamba, even minor improvements in yield and/or 2,5-regioselectivity of intermediate 2,5-dichlorophenol may provide a benefit for the overall yield of final products such as dicamba.

It has now been found that by using alkali metal sulfite and alkali metal hydroxide for the hydrolysis reaction of 1,2,4-trihalobenzene the process can be carried out in the substantial or even complete absence of organic solvents obtaining good yields of 2,5-dihalophenol. It has also been found that 2,5-regioselectivity can be improved under certain reaction conditions as described in further detail below.

In some embodiments of the present invention, about one molar equivalent of the compound of formula (II) is reacted in the presence of about 1.0 to about 1.4 molar equivalents of the alkali metal sulfite of formula $X_2SO_3$. Optionally, about one molar equivalent of the compound of formula (II) is reacted in the presence of about 1.1 to about 1.3 molar equivalents of an alkali metal sulfite of formula $X_2SO_3$.

In a further embodiment of the present invention, about one molar equivalent of the compound of formula (II) is reacted in the presence of about 0.5 to about 4.0 molar equivalents of an alkali metal hydroxide of formula YOH. Optionally, about one molar equivalent of the compound of formula (II) is reacted in the presence of about 1.2 to about 2.0 molar equivalents of an alkali metal hydroxide of formula YOH.

In another embodiment, about one molar equivalent of the compound of formula (II) is reacted in the presence of about 20 to about 40 molar equivalents of water. Optionally, about one molar equivalent of the compound of formula (II) is reacted in the presence of about 25 to 38 molar equivalents of water.

As mentioned above, the process can be carried out in the substantial or complete absence of organic solvent, while minor amounts of $C_1$-$C_4$ alcohol may be present. In this embodiment, the above process may be carried out in the optional presence of up to 3 molar equivalents of a $C_1$-$C_4$ alcohol per about one molar equivalent of the compound of formula (II). Optionally, from 0 to 2 molar equivalents of a $C_1$-$C_4$ alcohol are employed in case that any alcohol is present. Suitable $C_1$-$C_4$ alcohols may include methanol, ethanol, iso-propanol, n-propanol, n-butanol, iso-butanol and tert-butanol, e.g. methanol, if an alcohol is present at all. In another embodiment, the process is carried out without using alcohols and in the complete absence of any other organic solvents.

The step of reacting the compound of formula (II) can be carried out at a temperature of at least about 250° C. Optionally, the process is carried out at a temperature of at least about 265° C., or at least about 270° C., such as at about 250° C. to about 290° C., or about 265° C. to about 290° C., or about 270° C. to about 290° C.

Furthermore, the step of reacting the compound of formula (II) is typically carried out at increased pressure. In some embodiments, the step of reacting the compound of formula (II) is carried out at a pressure of about 2050 kPa to about 5600 kPa. Optionally, the process is carried out at a pressure of about 3500 kPa to about 5370 kPa, e.g. at about 4820 kPa to about 5350 kPa.

As already mentioned above, alkali metal phenolates which may be obtained in the above described reaction step can be converted into the corresponding compounds of formula (I) by means of acidification, e.g. using a suitable acid such as $H_2SO_4$ or HCl.

The hydrolyzation product of compounds of formula (I) according to the present invention can represent a valuable final product or an intermediate for chemical synthesis of other compounds. Thus, the hydrolyzation product of formula (I) can be further reacted to obtain other valuable chemicals or intermediates. In a specific embodiment of the present invention the compound of formula (I) is reacted to obtain a compound of formula (III)

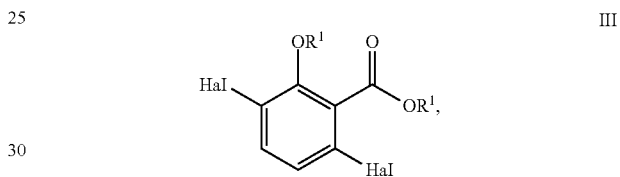

wherein Hal is as defined above, and $R^1$ is an alkali metal.

The above reaction from compounds of formula (I) to compounds of formula (III) is known in the art as the "Kolbe-Schmitt reaction". Reactions under Kolbe-Schmitt conditions can be carried out on an industrial scale in good yields. For example, the above conversion is part of known reaction sequences for obtaining dicamba from 2,5-dichlorophenol. The reaction is typically carried out in the presence of an alkali metal hydroxide and carbon dioxide.

In another embodiment, the compound of formula (III) is used to obtain a compound of formula (IV)

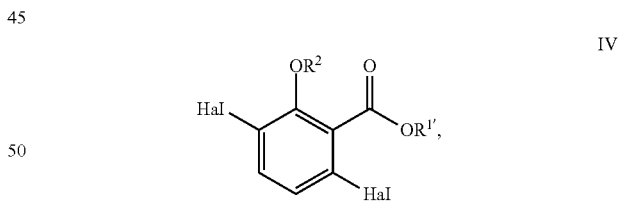

wherein $R^2$ is —$(C_1$-$C_4)$alkyl, $R^{1'}$ is an alkali metal or is —$(C_1$-$C_4)$alkyl, and Hal is as defined above. For example, $R^{1'}$ is identical to $R^2$. In this embodiment, the carboxylic group may partly be converted to the corresponding ester and may partly remain in deprotonated from. Since dicamba, which exhibits a free carboxylic acid group, is a preferred reaction product according to the present invention, it is not detrimental in this reaction step if the carboxylic acid group is only partly converted. Rather, final end products containing a free carboxylic acid group can also be obtained in subsequent reaction steps, as described below.

For example, in a further embodiment according to the invention, the compound of formula (IV) is converted to the corresponding carboxylic acid by hydrolyzing an ester of formula (IV) (i.e. wherein $R^{1'}$ is —$(C_1$-$C_4)$alkyl) under basic conditions, and is subsequently acidified to obtain a compound of formula (V)

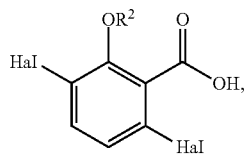

wherein $R^2$ and Hal are as defined above.

The above reaction step can be carried out analogously to prior art reactions sequences for obtaining dicamba from 2,5-dichlorophenol in good yields, e.g. on an industrial scale.

In specific embodiments according to the invention, X and/or Y are selected from the group consisting of sodium or potassium. For example, X and/or Y are sodium. In one embodiment, X and Y are sodium. Thus, the alkali metal hydroxide of formula YOH used for the hydrolyzation reaction for obtaining the compound of formula (I) can be potassium hydroxide or sodium hydroxide, e.g. sodium hydroxide. Furthermore, the alkali metal sulfite of formula $X_2SO_3$ can be $Na_2SO_3$ or $K_2SO_3$, e.g. $Na_2SO_3$.

In some embodiments, $R^1$ is selected from sodium and potassium. $R^1$ is derived from an alkali metal hydroxide, e.g. sodium hydroxide or potassium hydroxide used during the Kolbe-Schmitt reaction step. In some embodiments, it may be advantageous to replace one alkali metal with another alkali metal as described below. In one embodiment, $R^1$ is potassium in the above-described Kolbe-Schmitt reaction step, e.g. KOH is used in the step of providing the compound of formula (III).

In further embodiments according to the present invention, in case $R^{1'}$ is not an alkali metal in the compound of formula (IV) described above, $R^{1'}$ is ethyl or methyl. In these embodiments, $R^{1'}$ can be identical to $R^2$. $R^2$ is, according to some embodiments, also selected from ethyl and methyl. In a specific embodiment, $R^2$ is methyl. In such a specific embodiment $R^{1'}$ can also be methyl in case it is not an alkali metal. In case $R^{1'}$ is an alkali metal, it may be identical to $R^1$ as defined above, or is an alkali metal different from $R^1$, i.e. can be different in different reaction steps. For example, $R^{1'}$ may be Na or may be identical to $R^2$.

In specific embodiments, the processes according to the present invention are used in the synthesis of dicamba. In these embodiments, the compound of formula (V) is

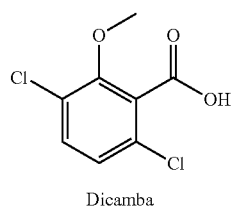

Dicamba

Further embodiments of the present invention are apparent from the following detailed description and the attached claim set.

DETAILED DESCRIPTION OF THE INVENTION

In the following, illustrative embodiments of the present invention are described in more detail.

The term "Hal" or "halogen" as used herein refers to a halogen atom independently selected from F, Cl, Br and I. For example, Hal is independently selected from Cl and Br. In specific embodiments both substituents Hal are identical. For example, both substituents are Cl.

The present invention relates to a process for hydrolyzing a compound of formula (II) to obtain a corresponding phenol of formula (I) which can be carried out in the absence of organic solvents. According to some embodiments, the process can be carried out under conditions for obtaining improved regioselectivity.

The prior art describes hydrolyzation of 1,2,4-trihalobenzenes, such as 1,2,4-trichlorobenzene, by using NaOH in solution in an alcoholic solvent. For example, hydrolyzation of 1,2,4-trichlorobenzene with NaOH in methanol affords 2,5-dichlorophenol. By following this prior art approach several byproducts may be obtained, including 2,5-dichlorophenol methyl ether, 2,4-dichlorophenol methyl ether, 3,4-dichlorophenol methyl ether, 2,4-dichlorophenol, and 3,4-dichlorophenol. The 2,5-regioselectivity obtained in the above reaction according to the prior art is about 70%.

The term "2,5-regioselectivity" as used in the context of the present invention refers to the ratio of the amount of 2,5-dihalophenol to the total amount of 2,5-dihalophenol, 2,4-dihalophenol, and 3,4-dihalophenol obtained in the reaction. On the other hand, the term "2,5-regioselectivity" employed above in connection with prior art processes for obtaining 2,5-dichlorophenol from 1,2,4-trichlorobenzene using NaOH in methanol refers to the combined amounts of 2,5-dichlorophenol and 2,5-dichlorophenol methyl ether to the total amount of 2,5-dichlorophenol, 2,5-dichlorophenol methyl ether, 2,4-dichlorophenol, 2,4-dichlorophenol methyl ether, 3,4-dichlorophenol, and 3,4-dichlorophenol methyl ether obtained.

Analogously, the term "2,4-regioselectivity" refers in the context of the present invention to the ratio of the amount of 2,4-dihalophenol to the total amount of 2,5-dihalophenol, 2,4-dihalophenol, and 3,4-dihalophenol obtained.

In addition, the term "3,4-regioselectivity" refers in the context of the present invention to ratio of the amount of 3,4-dihalophenol to the total amount of 2,5-dihalophenol, 2,4-dihalophenol, and 3,4-dihalophenol obtained.

In the context of the present invention it can be desired to reduce the degree of 2,4-regioselectivity and 3,4-regioselectivity. A specific product obtainable in the processes according to the invention is 2,5-dichlorophenol which can e.g. be used for the production of dicamba.

The term "alkali metal" when used in the context of the present invention refers to lithium, sodium or potassium. Sodium and potassium are specific examples.

Thus, the present invention relates to a process for hydrolyzing 1,2,4-trihalbenzene of formula (II) to obtain a compound of formula (I):

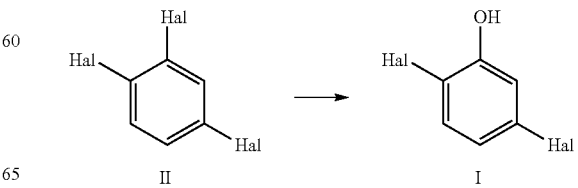

II → I wherein Hal is a halogen, in the presence of an alkali metal sulfite, an alkali metal hydroxide and water as described above, which can be carried out in the absence of organic solvents.

The reaction is typically carried out in a pressure reactor. In such an exemplary embodiment, the reactants are added to the pressure reactor, the pressure reactor is sealed and subsequently heated to the desired reaction temperature during which the pressure in the pressure reactor increases. After the desired reaction time, the pressure reactor can be cooled to room temperature. The product can be isolated by adding a suitable solvent, such as an ether (e.g. methyl tert.-butyl ether) or methylene chloride ($CH_2Cl_2$), transferring the reaction mixture into a separation device, such as a separation funnel, acidifying the mixture using a suitable acid such a $H_2SO_4$ or HCl to a pH of e.g. less than 1.5, and extracting the mixture using a suitable organic solvent, such as an ether (e.g. methyl tert.-butyl ether) or methylene chloride ($CH_2Cl_2$). Continuous extraction in a suitable device or sequential extraction (e.g. three times) can be employed.

The reaction temperature is typically at least 250° C., optionally at least about 265° C., further optionally at least about 270° C., such as about 250° C. to about 290° C., or about 265° C. to about 290° C., or about 270° C. to about 290° C. In particular, the reaction temperature is selected so that the 2,5-regioselectivity can be improved.

The pressure within the pressure vessel is typically about 2050 kPa to about 5600 kPa. The pressure may depend on parameters such as reaction temperature, time, amount of water added, and amount of alcohol, if added at all.

The reaction time is typically 4 hours or less. In an exemplary embodiment, the reaction time is from 2 hours to 3.5 hours.

In a further embodiment, the compound of formula (I) is converted into valuable chemical products or intermediates. In a specific embodiment, the compound of formula (I) is subjected to a carboxylation reaction under Kolbe-Schmitt conditions to obtain a compound of formula (III).

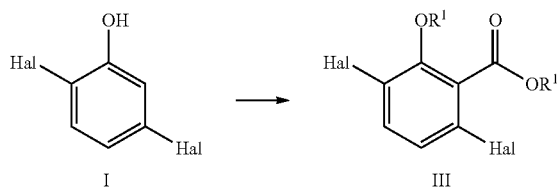

In the carboxylation step, the compound of formula (I) is first converted into the corresponding phenolate by treating with an alkali metal hydroxide $R^1OH$. $R^1OH$ can be sodium hydroxide or potassium hydroxide, e.g. potassium hydroxide. The alkali metal hydroxide can be used in about stoichiometric amounts in an aqueous solution having e.g. a concentration of 50 wt.-%. The conversion can be carried out in a suitable organic solvent such as xylene. Water can be removed from the system using azeotropic distillation.

Subsequently, the phenolate is contacted with gaseous $CO_2$ under high pressure. The phenolate solution in e.g. xylene can be used without further workup. The reaction affords the carboxylic acid salt of formula (III), which normally is not soluble in the reaction medium such as xylene but is soluble in water and, therefore, can easily be separated.

In a further embodiment, the compound of formula (III) is alkylated to obtain a compound of formula (IV).

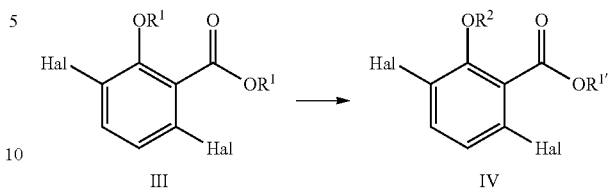

The reaction is accomplished by reacting the compound of formula (III) with an alkyl halide of formula $ZR^2$, wherein Z is halogen, such as Cl, Br or I, and $R^2$ is as defined above. In particular, Z can be Cl or Br, e.g. Cl. In one embodiment, the alkyl halide is methyl chloride. The reaction can be carried out in aqueous solution. During the reaction, the pH, temperature and pressure may be controlled such that the reaction is carried out at a pH of 8 to 12, a temperature of about 90° C. to about 100° C. and/or a pressure of about 500 to about 1050 kPa. An excess of alkyl halide is usually used. Thus, the compound of formula (IV) can be partly esterified. In this case, $R^{1'}$ is identical to $R^2$.

Furthermore, if deemed appropriate to increase solubility of the compound of formula (IV), the double salt may be converted in advance of the reaction to a corresponding mixed salt by treating with an alkali metal hydroxide different from the alkali metal hydroxide used in the previous reaction step. For example, when potassium hydroxide is used in the Kolbe-Schmitt reaction step, the compound of formula (IV) may be treated with sodium hydroxide in advance of the alkylation step to obtain a mixed potassium/sodium salt. In these cases, $R^{1'}$ may be an alkali metal different from $R^1$. In other cases, $R^{1'}$ can be identical to $R^1$.

In a further embodiment, the compound of formula (IV) is converted to the compound of formula (V).

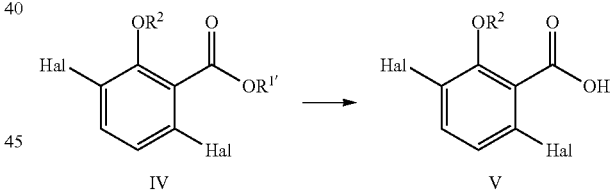

In cases where the compounds of formula (IV) include an ester in which $R^{1'}$ is identical to $R^2$, the ester can be hydrolyzed under basic conditions using a suitable base to obtain the corresponding carboxylic acid salts. For example, alkali metal hydroxides such as NaOH may be employed here. Compounds of formula (IV) in which $R^{1'}$ is an alkali metal may be present during hydrolysis without harm. Thus, a composition comprising a compound of formula (IV) in which $R^{1'}$ is an alkali metal, such as sodium, is obtained.

The alkali metal salt of formula (IV) can then be acidified in solution using a suitable acid, such as $H_2SO_4$ or HCl, e.g. HCl, to afford the compound of formula (V). In cases where a compound of formula (IV) in which $R^{1'}$ is an alkali metal is obtained in the previous reaction step, the composition can be directly subjected to acidification without the above hydrolyzation.

Although the processes according to the embodiment as described above can be employed for providing a variety of final products and intermediates, the present invention will be illustrated by describing a sequence of reaction steps for obtaining dicamba starting from 1,2,4-trichlorobenzene. A person skilled in the art will comprehend that certain reaction steps in this sequence are preferred as opposed to essential, and will further be able to adapt the processes described herein for the production of other compounds and intermediates within the scope of the appended claims.

In a specific embodiment, the present invention provides a process for obtaining dicamba starting from 1,2,4-trichlorobenzene. In this embodiment, in a first step of the reaction sequence, 1,2,4-trichlorobenzene is subjected to a hydrolyzation reaction using sodium hydroxide and sodium sulfite in the presence of water at a temperature of 270° C. or more and a pressure of 4820 kPa to 5350 kPa as described above to obtain 2,5-dichlorophenol.

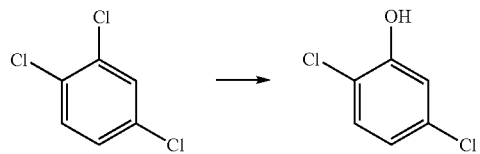 [SMILES: Clc1ccc(Cl)c(Cl)c1 ; Oc1cc(Cl)ccc1Cl]

1,2,4-trichlorobenzene is a compound within the definition of formula (II) as defined above, in which Hal is Cl. Furthermore, 2,5-dichlorophenol is a compound within the definition of formula (I) according to the present invention, in which Hal is Cl.

According to some embodiments of the invention, 2,5-dichlorophenol is further subjected to carboxylation under Kolbe-Schmitt conditions using KOH and $CO_2$ as described above to obtain the dipotassium salt of 3,6-dichlorosalicylic acid.

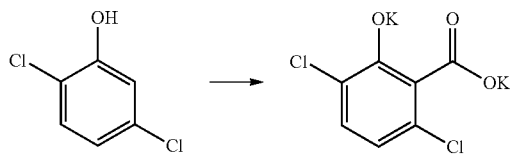

The dipotassium salt of 3,6-dichlorosalicylic acid is a compound according to formula (III) of the present invention, in which Hal is Cl, and $R^1$ is K.

In one embodiment, the dipotassium salt of 3,6-dichlorosalicylic acid is methylated in a subsequent reaction step using methyl chloride. As described above, this conversion may include converting the dipotassium salt into a mixed salt in order to improve solubility in water. NaOH can be used for the provision of the mixed salt. Methylation of dipotassium 3,6-dichlorosalicylic acid after conversion into a mixed salt typically affords a mixture of the sodium and/or potassium form of 3,6-dichloro-2-methoxybenzoic acid and 3,6-dichloro-2-methoxybenzoic acid methyl ester.

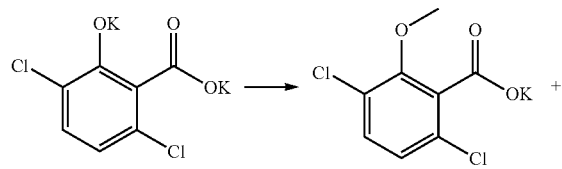

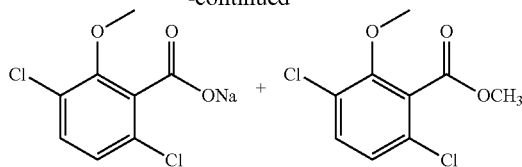

The product obtained in the reaction described above is a compound according to formula (IV) of the present invention in which Hal is Cl, $R^2$ is methyl, and $R^{1'}$ is either K, Na or methyl.

The above mixture can subsequently be converted to dicamba by hydrolyzing the ester compounds in the mixture using NaOH as described above and subsequently acidifying the resulting product using HCl as outlined above.

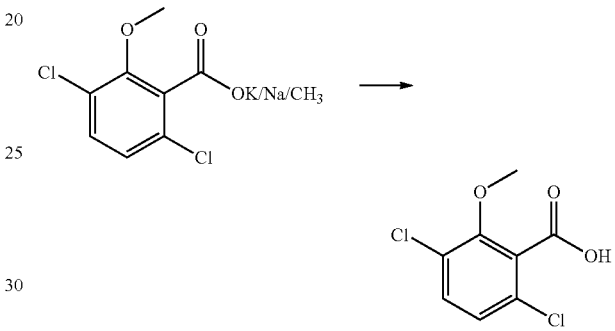

Dicamba is a compound according to formula (V) of the present invention, in which Hal is Cl, and $R^2$ is methyl.

The above reaction sequence can be carried out on an industrial scale. The first process step of the sequence is typically carried out in the absence of organic solvents. Furthermore, the present invention provides in some embodiments a synthetic route to dicamba starting from 1,2,4-trichlorobenzene with improved 2,5-regioselectivity, which is suitable to be carried out on an industrial scale.

EXAMPLES

The present invention will be further illustrated by means of a comparative example and working examples.

1. Comparative Example 1,2,4-trichlorobenzene (TCB), NaOH (in the form of a 50 wt-% solution in water) and methanol were charged into a pressure reactor. The molar ratio of TCB:NaOH:methanol was 1.0:2.4:10. Afterwards, the pressure reactor was sealed, heated to 190° C. under agitation and held at this temperature for 90 minutes. During the reaction, agitation was continued. The reactor was then cooled to room temperature using an ice-$H_2O$ bath.

The reaction mixture was then transferred into a separation funnel and acidified with 10% $H_2SO_4$ to a pH of below 1.5. The aqueous layer of the resulting two-layer mixture was then extracted three times with methylene chloride.

The obtained yield of 2,5-dichlorophenol was 64.6%. The obtained regioselectivity (2,5-dichlorophenol and 2,5-dichlorophenol methyl ether/2,4-dichlorophenol and 2,4-dichlorophenol methyl ether/3,4-dichlorophenol and 3,4-dichlorophenol methyl ether) was 71.9/15.5/12.6 (analysis using GC).

2. Working Example 1

1,2,4-trichlorobenzene (TCB), NaOH, $Na_2SO_3$ and water were charged into a pressure reactor. Apart from minor amounts of methanol the reaction was carried out in the absence of organic solvents. The molar ratio of TCB:NaOH:$Na_2SO_3$:$H_2O$: methanol was 1.0:2.2:1.2:37.2:2.0. Afterwards, the pressure reactor was sealed, heated to 250° C. and held at this temperature for 2 hours (final pressure 4140 kPa). 2,5-Dichlorophenol was obtained as the product in good yield and 2,5-regioselectivity. The product was extracted using $CH_2Cl_2$.

3. Working Example 2

1,2,4-trichlorobenzene (TCB), NaOH, $Na_2SO_3$ and water were charged into a pressure reactor in the absence of organic solvents. The molar ratio of TCB:NaOH:$Na_2SO_3$:$H_2O$ was 1.0:2.0:1.2:37.7. Afterwards, the pressure reactor was sealed, heated to 250° C. and held at this temperature for 2 hours (final pressure of 3620 kPa). 2,5-Dichlorophenol was obtained as the product in good yield and 2,5-regioselectivity. The product was extracted using $CH_2Cl_2$.

4. Working Example 3

1,2,4-trichlorobenzene (TCB), NaOH, $Na_2SO_3$ and water were charged into a pressure reactor in the absence of organic solvents. The molar ratio of TCB:NaOH:$Na_2SO_3$:$H_2O$ was 1.0:1.2:1.2:37.7. Afterwards, the pressure reactor was sealed, heated to 270° C. and held at this temperature for 2 hours (final pressure of 5345 kPa). 2,5-Dichlorophenol was obtained as the product in good yield and a 2,5-regioselectivity of 90.2%. The product was extracted using $CH_2Cl_2$.

5. Working Example 4

1,2,4-trichlorobenzene (TCB), NaOH, $Na_2SO_3$ and water were charged into a pressure reactor in the absence of organic solvents. The molar ratio of TCB:NaOH:$Na_2SO_3$:$H_2O$ was 1.0:2.0:1.2:27.8. Afterwards, the pressure reactor was sealed, heated to 270° C. and held at this temperature for 2 hours (final pressure of 4825 kPa). 2,5-Dichlorophenol was obtained as the product in good yield and a 2,5-regioselectivity of 94.3%. The product was extracted using $CH_2Cl_2$.

The invention claimed is:
1. A process for providing a compound of formula (I):

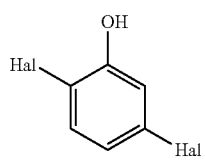

wherein Hal is a halogen,
the process comprising the step of:
reacting a compound of formula (II)

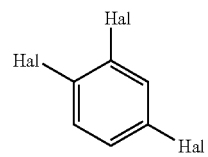

wherein Hal is defined as above,
with an alkali metal sulfite of the formula $X_2SO_3$ and an alkali metal hydroxide of the formula YOH, wherein X and Y are independently selected from an alkali metal.

2. The process of claim 1, wherein the process is carried out in the presence of water.

3. The process of claim 2, wherein the process is carried out in the presence of a $C_1$-$C_4$ alcohol.

4. The process of claim 3, wherein the process is carried in the absence of organic solvents apart from the optional presence of a $C_1$-$C_4$ alcohol.

5. The process of claim 1, wherein the process is carried out in in the absence of organic solvents.

6. The process of claim 1, wherein about one molar equivalent of the compound of formula (II) is reacted in the presence of
   (a) about 1.0 to about 1.4 molar equivalents of an alkali metal sulfite of formula $X_2SO_3$, wherein X is as defined in claim 1; and/or
   (b) about 0.5 to about 4.0 molar equivalents of an alkali metal hydroxide of formula YOH, wherein Y is as defined in claim 1; and/or
   (c) about 20 to about 40 molar equivalents of water; and/or
   (d) up to 3 molar equivalents of a $C_1$-$C_4$ alcohol, wherein apart from the $C_1$-$C_4$ alcohol no further organic solvent is present.

7. The process of claim 1, wherein the step of reacting the compound of formula (II) is carried out at a
   (a) temperature of at least about 250° C.; and/or
   (b) pressure of about 2050 kPa to about 5600 kPa.

8. The process of claim 1, further comprising the step of reacting the compound of formula (I) to obtain a compound of formula (III)

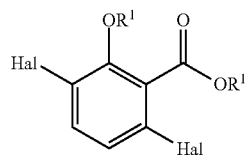

wherein Hal is as defined in claim 1, and $R^1$ is an alkali metal.

9. The process of claim 8, wherein the step of reacting the compound of formula (I) to obtain a compound of formula (III) is carried out in the presence of an alkali metal hydroxide and carbon dioxide.

10. The process of claim 8, further comprising the step of reacting the compound of formula (III) to obtain a compound of formula (IV)

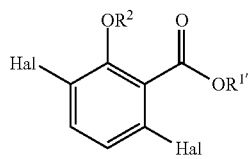

IV wherein $R^2$ is —$(C_1-C_4)$alkyl, R" is an alkali metal or —$(C_1-C_4)$alkyl, and Hal is a halogen.

11. The process of claim 10, further comprising the step of reacting the compound of formula (IV) to obtain a compound of formula (V)

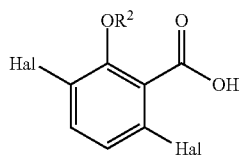

V wherein $R^2$ and Hal are as defined in claim 10.

12. The process of claim 1, wherein
(a) Hal is selected from the group consisting of F, Cl, Br and I; and/or
(b) X and Y are independently selected from sodium or potassium; and/or
(c) $R^1$ is selected from sodium and potassium; and/or
(d) $R^{1'}$ is selected from sodium and potassium, or $R^{1'}$ is selected from ethyl and methyl.

13. The process of claim 11, wherein the compound of formula (V) is

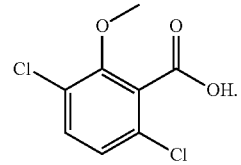

14. The process of claim 13, wherein the process is carried out in the presence of water.

15. The process of claim 14, wherein the process is carried out in the presence of a $C_1-C_4$ alcohol.

16. The process of claim 15, wherein the process is carried in the absence of organic solvents apart from the optional presence of a $C_1-C_4$ alcohol.

17. The process of claim 13, wherein the process is carried out in in the absence of organic solvents.

18. The process of claim 7, wherein the step of reacting the compound of formula (II) is carried out at a temperature of at least about 265° C.

19. The process of claim 7, wherein the step of reacting the compound of formula (II) is carried out at a temperature of about 265° C. to about 290° C.

* * * * *